(12) United States Patent
Kwon

(10) Patent No.: US 11,771,726 B2
(45) Date of Patent: Oct. 3, 2023

(54) COMPOSITION, CONTAINING QUISQUALIS INDICA EXTRACT, FOR PREVENTING OR TREATING PROSTATIC HYPERPLASIA

(71) Applicant: The Industry & Academic Cooperation in Chungnam National University (IAC), Daejeon (KR)

(72) Inventor: Hyo Jung Kwon, Yuseong-gu (KR)

(73) Assignee: The Industry & Academic Cooperation in Chungnam National University, Daejeon (KR)

( * ) Notice: Subject to any disclaimer, the term of this patent is extended or adjusted under 35 U.S.C. 154(b) by 28 days.

(21) Appl. No.: 16/725,608

(22) Filed: Dec. 23, 2019

(65) Prior Publication Data

US 2020/0138886 A1 May 7, 2020

Related U.S. Application Data

(62) Division of application No. 15/574,702, filed as application No. PCT/KR2016/004653 on May 3, 2016, now abandoned.

(30) Foreign Application Priority Data

May 18, 2015 (KR) .......................... 10-2015-0069047

(51) Int. Cl.
*A61K 36/185* (2006.01)
*A61P 13/08* (2006.01)

(52) U.S. Cl.
CPC ............ *A61K 36/185* (2013.01); *A61P 13/08* (2018.01)

(58) Field of Classification Search
None
See application file for complete search history.

(56) References Cited

U.S. PATENT DOCUMENTS

| 4,377,584 A | 3/1983 | Rasmusson et al. |
| 4,760,071 A | 7/1988 | Rasmusson et al. |
| 6,211,198 B1 * | 4/2001 | Gluchowski ......... C07D 211/90 514/318 |
| 7,084,274 B2 | 8/2006 | Moon et al. |
| 2002/0151503 A1 | 10/2002 | Slusher et al. |
| 2012/0270837 A1 | 10/2012 | Tripp et al. |
| 2014/0349953 A1 | 11/2014 | Nishida et al. |
| 2016/0058782 A1 | 3/2016 | Nishida et al. |

FOREIGN PATENT DOCUMENTS

| CN | 1221346 A | * 6/1999 | ............. A61K 31/00 |
| CN | 1221346 A | 6/1999 | |
| CN | 1883521 A | 12/2006 | |
| CN | 1020287789 A | 4/2011 | |
| CN | 103479978 A | 1/2014 | |
| CN | 104114176 A | 10/2014 | |
| CN | 104171635 A | 12/2014 | |
| CN | 104586664 A | 5/2015 | |
| JP | 3176983 B2 | 6/2001 | |
| JP | 2003040769 A | 2/2003 | |
| JP | 2006-199609 A | 8/2006 | |
| KR | 1020130013712 | 2/2013 | |
| KR | 1020150048495 | 5/2015 | |

OTHER PUBLICATIONS

Sahu et al. ("Quisqulis indica Linn: A Review of its Medicinal Properties", Int.J.Pharm.Phytopharmacol.Res. 2012, 1(5): 313-321) (Year: 2012).*
Inernational Search report in PCT/KR2016/004653, dated May 3, 2016.
U.S. Office action in U.S. Appl. No. 15/574,702 dated Mar. 19, 2019.
Charith UB Wijerathne et al., Quisqualis indica Improves Benign Prostatic Hyperplasia by Regulating Prostate Cell Proliferation and Apoptosis, 2017, Biol. Pharm. Bull., vol. 40, pp. 2125-2133.
Qianliang, L., "Chinese Medicine", Chinal Phamaceutical Science and Technology Press, 1st Edition, Aug. 1992, 146-147.
Australian Government Department of Health and Ageing Therapeautic Goods Administration, CMEC 70 Complementary Medicines Evaluation Committee, Dec. 12, 2008.
Attachment 3, Item 7.1, CMEC 70 Complementary Medicines Evaluation Committee, Email correspondence to the TGA received from Dharamanada Subhuti, Oct. 2008.

* cited by examiner

*Primary Examiner* — Michael Barker
*Assistant Examiner* — Randall O Winston
(74) *Attorney, Agent, or Firm* — Schott, P.C.

(57) ABSTRACT

A pharmaceutical composition comprises a *Quisqualis indica* extract as an active ingredient, for preventing or treating prostatic hyperplasia, and may also be used in a food composition. The *Quisqualis indica* extract may be used to treat and prevent prostatic hyperplasia by exhibiting effects of a reduction in prostate weight, a reduction in DHT as a prostatic hyperplasia inducing factor, and a reduction in prostate epithelial cell hyperplasia.

5 Claims, 5 Drawing Sheets

COMPOSITION, CONTAINING QUISQUALIS INDICA EXTRACT, FOR PREVENTING OR TREATING PROSTATIC HYPERPLASIA

BACKGROUND

Benign prostatic hyperplasia (BPH) is a male disease rapidly occurring in Korean men aged 50 years or older, and recently the number of patients with benign prostatic hyperplasia in Korea is sharply increasing over 20% per year. In the case of this disease, the cause is the overgrowth of smooth cell and epithelial cell in the transition zone of prostate, and various urinary disorders caused by bladder obstruction occur. It is known that one mechanism of prostatic hyperplasia is related to male hormones, testosterone and dihydrotestosterone (DHT).

Meanwhile, among drugs for treating prostatic hyperplasia, 5-alpha reductase inhibitor expresses an anti-androgenic activity effect by selectively inhibiting the generation of dihydrotestosterone while not affecting testosterone having male hormone activities, and reduces the enlarged prostate without side effects appearing in anticancer hormone drugs, so it is recognized as a drug for safe and causal treatment of urinary disorders. Accordingly, a compound such as finasteride (Proxcar, Merck) which inhibits the generation of dihydrotestosterone in tissue by inhibiting the activity of 5-alpha reductase enzyme is commercially available as a drug for treating prostatic hyperplasia (U.S. Pat. Nos. 4,377,584, 4,760,071, Korean Patent Publication No. 2004-0016559).

*Quisqualis indica* is native to India, and grows in southern regions of China and tropical regions. The common name of *Quisqualis indica* comes from the person called Guo Shijun in a certain province of China, which was told by later generations of medical practitioners that he treated many children's diseases with this drug alone. It has warm properties and tastes sweet, and contains quiscalic acid, triggonelline, pyridine and fatty oil as active ingredients. It is used to kill parasites, and its percentage amounts to about 70%. Besides, it is used to treat roundworms, but its effect is lower than one of killing parasites, and it functions to strengthen stomachs even though its effect is weak. This drug is less toxic, causing no damage to bodies, and is known as being good for children to eat because it tastes sweet (Encyclopedia of Korean Culture).

However, the treatment effect of the *Quisqualis indica* extract for prostatic hyperplasia has been referred to or disclosed nowhere in papers reported so far.

While the inventors are in continuous research to develop natural medicinal substances having an effect of inhibiting prostatic hyperplasia, they discovered the fact that a *Quisqualis indica* extract has a good effect in improving prostatic hyperplasia that has never been reported so far in relation to the prostatic hyperplasia treatment effect, and have completed the present disclosure.

SUMMARY OF THE EMBODIMENTS

Therefore, the present disclosure is directed to providing a pharmaceutical composition comprising a *Quisqualis indica* extract for preventing or treating prostatic hyperplasia, as a natural medicinal substance having effects on the reduction of prostate weight, DHT and epithelial hyperplasia in prostatic hyperplasia.

The present disclosure is further directed to providing a food composition comprising the extract.

Technical Solution

According to one aspect of the present disclosure, the present disclosure provides a pharmaceutical composition comprising a *Quisqualis indica* extract as an active ingredient for preventing or treating prostatic hyperplasia.

In the present disclosure, the *Quisqualis indica* extract includes all extracts prepared with a whole or part of the plant body by a common plant extraction method known in the art. Preferably, the *Quisqualis indica* extract is a crude extract, a polar solvent soluble extract, or a non-polar solvent soluble extract.

After milled, the *Quisqualis indica* material of the present disclosure is extracted using a polar solvent selected from water, ethanol, lower alcohol having 1 to 4 carbon atoms or their mixed solvent, preferably water or a mixed solvent of water and ethanol, and more preferably, water or a mixed solvent of 1 to 30% (v/v) water and ethanol, whose volumes are about 1 to 100 times, preferably about 2 to 20 times, greater than the sample weight, at 20 to 120° C., preferably 30 to 80° C. for about 1 to about 72 hours, preferably 2 to 12 hours by an extraction method such as hydrothermal extraction, cold extraction, reflux extraction or ultrasonic extraction, preferably hydrothermal extraction, followed by reduced pressure filtration and concentration, to obtain the *Quisqualis indica* extract of the present disclosure.

In the preferred embodiment of the present disclosure, it is found out that the *Quisqualis indica* extract has effects on the reduction of prostate weight, DHT which is a factor causing benign prostatic hyperplasia, and prostate epithelial hyperplasia, and thus is effective in treating and preventing prostatic hyperplasia.

Accordingly, the present disclosure provides a pharmaceutical composition or a food composition comprising the *Quisqualis indica* extract as an active ingredient for preventing or treating prostatic hyperplasia.

Furthermore, because a *Quisqualis indica* extract is a medicinal substance that has been long eaten or used as herb medication, the extracts of the present disclosure extracted therefrom also have no toxicity and side effect problem.

The pharmaceutical composition comprising the extract of the present disclosure for preventing or treating prostatic hyperplasia may include the extract in an amount of 0.1 to 50 weight % based on the total weight of the composition.

The pharmaceutical composition comprising the extract of the present disclosure may further include appropriate carriers, excipients and diluents commonly used to prepare pharmaceutical compositions.

The pharmaceutical dosage form of the extract of the present disclosure may be also used in the form of their pharmaceutically acceptable salt, and may be used alone or in combination with other pharmaceutically active compounds, and used as appropriate mixtures.

The pharmaceutical composition comprising the extract according to the present disclosure may be formulated and used by each common method as oral dosage formulations such as powders, granules, tablets, capsules, suspensions, emulsions, syrups and aerosols, external applications, suppositories and sterilized injection solutions. The carriers, excipients and diluents that may be included in the composition comprising the extract include lactose, dextrose, sucrose, sorbitol, mannitol, xylitol, erythritol, maltitol, starch, acacia rubber, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. In the case of formulation, the pharmaceutical composition is prepared using commonly used diluents or excipients such as fillers, extenders, binders, wetting agents, disintegrants and surfactants. A solid formulation for oral administration includes tablets, pills, powders, granules and capsules, and this solid formulation is prepared by mixing the extract with at least one excipient, for example, starch, calcium carbonate, sucrose or lactose, and gelatin. Furthermore, in addition to the excipients, lubricants such as magnesium stearate and talc are also used. A liquid formulation for oral use may include suspensions, solutions, emulsions and syrups, and may include commonly used diluents such as water, liquid paraffin as well as many excipients, for example, wetting agents, sweetening agents, flavoring agents and preservatives. The formulation for non-oral administration includes sterilized aqueous solutions, non-aqueous solvents, suspensions, emulsions, freeze-dried formulations and suppositories. For the non-aqueous solvents and suspensions, propyleneglycol, polyethylene glycol, vegetable oil such as olive oil, and injectable ester such as ethylolate may be used. For the suppository base, Witepsol, Macrogol, Tween 61, cacao butter, laurin fat and glycerogelatin may be used.

A preferable dose of the extract of the present disclosure changes depending on the patient's condition and weight, the degree of disease, the type of medication, and dosing route and period, but may be appropriately selected by those skilled in the art. However, for a preferable effect, the extract of the present disclosure is preferably administered at 0.0001 to 100 mg/kg, and preferably 0.001 to 100 mg/kg per day. Single or multiple doses per day may be used, and multiple divided doses may be used. The dose does not limit the scope of the present disclosure in any aspect.

The extract of the present disclosure may be administered via various routes. All predictable dosing methods can be used, and the extract may be administered via, for example, oral, rectal or intravenous, intramuscular, subcutaneous, epidural or intracerebroventricular injection route.

According to another embodiment of the present disclosure, the present disclosure provides a food composition comprising a *Quisqualis indica* extract as an active ingredient for preventing or improving prostatic hyperplasia.

In the present disclosure, the food composition is not limited to a particular type of food, and in its functional aspect, may be a health functional food. The "health functional food" refers to food prepared or processed using a raw material or ingredient having good functionality for human body in accordance with Article 6727 of the Health Functional Food Act, and "functional" refers to eating with an aim of obtaining a good effect for health purposes such as nutrient control or biological activity with regard to the structure and function of human body.

The food composition for preventing prostatic hyperplasia according to the present disclosure includes the extract in an amount of 0.01 to 95 weight %, and preferably 1 to 80 weight % based on the total weight of the composition.

Furthermore, for the purpose of prevention of prostatic hyperplasia, it is possible to prepare and process a health functional food in the form of tablets, capsules, powders, granules, liquids, and pills.

The food to which the extract of the present disclosure can be added includes, for example, different types of foods, beverage, gums, teas, vitamin complexes and health functional foods.

Furthermore, for the purpose of an effect on the prevention and improvement of prostatic hyperplasia, the extract may be added to the food or beverage. In this instance, an amount of the extract in the food or beverage may be 0.01 to 15 weight % based on the total food weight, and the extract may be added in an amount of 0.02 to 5 g, preferably 0.3 to 1 g, based on 100 ml of the beverage composition.

In addition to containing the extract as an essential ingredient in an indicated amount, the beverage composition of the present disclosure may contain other ingredients without any particular limitation, and like common beverage, may contain many flavoring agents or natural carbohydrates as an additional ingredient. Examples of the natural carbohydrate include monosaccharide, for example, glucose and fructose; disaccharide, for example, maltose and sucrose; and polysaccharide, for example, common sugar such as dextrin and cyclodextrin, and sugar alcohol such as xylitol, sorbitol and erythritol. For flavoring agents other than the foregoing, natural flavoring agents (thaumatin, stevia extracts (for example, rebaudioside A, glycyrrhizin, etc.) and synthetic flavoring agents (saccharin, aspartame, etc.) may be advantageously used. An amount of the natural carbohydrate is generally about 1 to 20 g, and preferably about 5 to 12 g based on 100 ml of the composition of the present disclosure.

In addition to the foregoing, the extract of the present disclosure may contain many nutritional supplements, vitamins, minerals (electrolytes), flavoring agents such as synthetic flavoring agents and natural flavoring agents, coloring agents and mogul agents (cheese, chocolate, etc.), pectic acid and its salt, alginic acid and its salt, organic acid, protective colloid thickening agents, pH regulating agents, stabilizing agents, preservatives, glycerin, alcohol, and carbonating agents used in carbonated beverage.

Advantageous Effects

As described above, the *Quisqualis indica* extract of the present disclosure can be usefully used to treat and prevent prostatic hyperplasia by virtue of the effects on the reduction of prostate weight, DHT which is a factor causing benign prostatic hyperplasia, and prostate epithelial hyperplasia.

DETAILED DESCRIPTION OF THE EMBODIMENTS

The present disclosure relates to a pharmaceutical composition comprising a *Quisqualis indica* extract as an active ingredient for preventing or treating prostatic hyperplasia, and to a food composition.

Hereinafter, the embodiments of the present disclosure will be described in detail. However, these embodiments are provided to describe the present disclosure in more detail and the scope of the present disclosure is not limited thereto.

Example 1

Preparation of *Quisqualis indica* Extract

After purchasing commercially available *Quisqualis indica* and milling it, 300 g was put into 3 L of 70% ethanol, and ultrasonic extraction was performed three times for 1 hour using an ultrasonic extractor. The extracted solution was filtered with Whatman No. 2 (150 mm φ) filter paper to remove insoluble materials, and concentrated under reduced pressure at 40° C. by a concentrator equipped with a cooled condenser. To completely remove the solvent, the reduced pressure concentrated extract was suspended with an addition of 500 mL of purified water, to obtain 80.51 g of extract using a freeze drier (yield: 26.84%).

Example 2

Animal Model

After 10-week old male Wister rats (Central Lab. Animal Inc.) were acclimated for a week, testosterone propionate (TP) was subcutaneously injected into the induced prostatic hyperplasia group at 3 mg/kg for 4 weeks to establish a model. The *Quisqualis indica* extract prepared in Example 1 was orally administered at 150 mg/kg for 4 weeks one hour before TP injection, and finasteride (10 mg/kg), a 5α-reductase enzyme inhibitor used to treat prostatic hyperplasia, was administered to the positive control group by the same method.

Statistical Analysis

Statistical analysis was conducted using ANOVA, ## $P<0.01$ and # $P<0.05$ indicate a significant difference compared to the normal control group (NC), and **$P<0.01$ and *$P<0.05$ indicate a significant difference compared to the induced prostatic hyperplasia group (BPH).

Example 3

Prostate Weight Measurements

After animal sacrifice, prostate was taken from each group (normal control group; NC, induced prostatic hyperplasia group; BPH, induced prostatic hyperplasia group+*Quisqualis indica* extract administered group; BPH+*Quisqualis indica*, induced prostatic hyperplasia group+finasteride administered group; BPH+finasteride), and its weight was measured.

Figure 1:
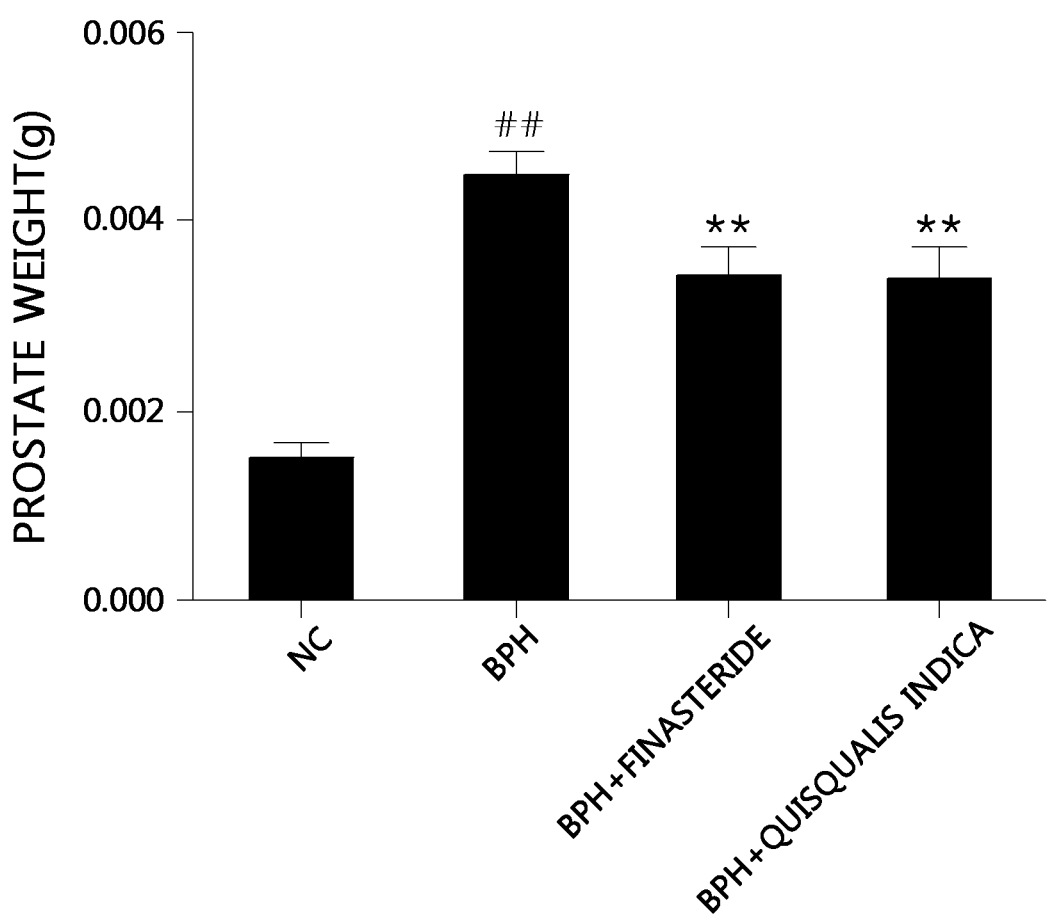
FIG. 1 shows prostate weight changes in prostatic hyperplasia animal models treated with the *Quisqualis indica* extract.

FIG. 1 shows prostate weight changes in prostatic hyperplasia animal models treated with the *Quisqualis indica* extract. As can be seen from FIG. 1, the prostate weight was significantly reduced in the *Quisqualis indica* extract administered group (BPH+*Quisqualis indica*) compared to the TP-induced prostatic hyperplasia group (BPH). This showed a similar effect to finasteride that is currently used to treat prostatic hyperplasia.

Example 4

Prostate DHT Changes

To measure changes in dihydrotestosterone (DHT) that is essential to generation, growth and maintenance of prostate, after the end of medication administration for 4 weeks, protein was separated from the prostate tissue dissociated at sacrifice. The prostate was put into RIPA buffer for extracting protein (20 mM Tris-HCl, 150 mM NaCl, 1 mM $Na_2EDTA$, 1 mM EGTA, 1% NP-40, 1% sodium deoxycholate, 2.5 mM sodium pyrophosphate, 1 mM b-glycerophosphate, 1 mM $Na_3VO_4$, 1 μg/ml leupeptin; Cell-Signaling, USA), followed by homogenation, and the homogenate was centrifugally separated at 1400 rpm for 15 minutes and the supernatant was collected. The concentration of the separated protein was measured using Bio-Rad protein assay kit (Bio-Rad, USA) and to measure the DHT concentration in the supernatant, an amount of DHT in prostate was measured according to the manufacturer's method using ELISA kit (Cayman, USA) that specifically responds to DHT. The measured value was converted based on quantitative protein value, and differences were compared by conducting statistical analysis.

Figure 2:
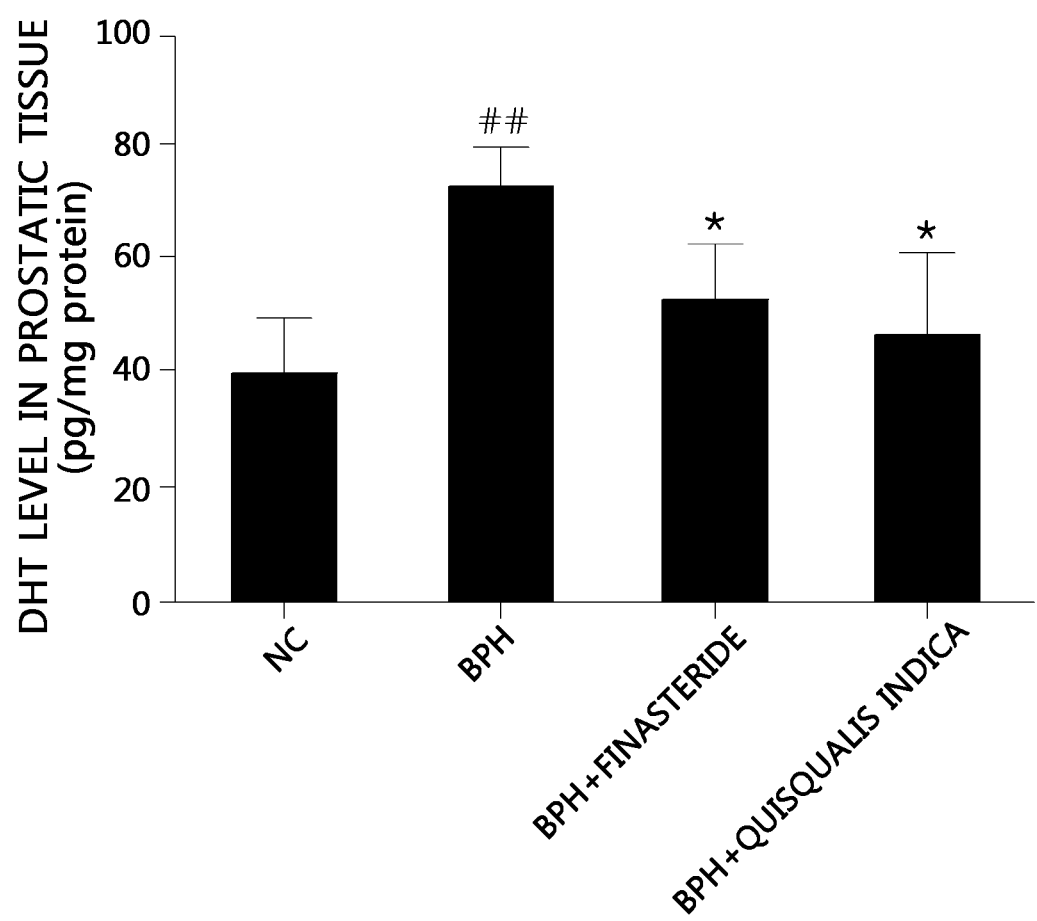
FIG. 2 shows prostate DHT changes in prostatic hyperplasia animal models treated with the *Quisqualis indica* extract.

FIG. 2 shows prostate DHT changes in prostatic hyperplasia animal models treated with the *Quisqualis indica* extract. As can be seen from FIG. 2, it was found that the concentration of DHT causing prostatic hyperplasia was significantly reduced in the group administered with the *Quisqualis indica* extract.

Example 5

Serum Testosterone Measurements

To determine the testosterone levels in the prostatic hyperplasia animal model, the blood separated after the end of the experiment was centrifugally separated at 12,000 rpm for 20 minutes, the supernatant was harvested and serum testosterone levels were measured using ELISA kit (Cayman, USA).

Figure 3:
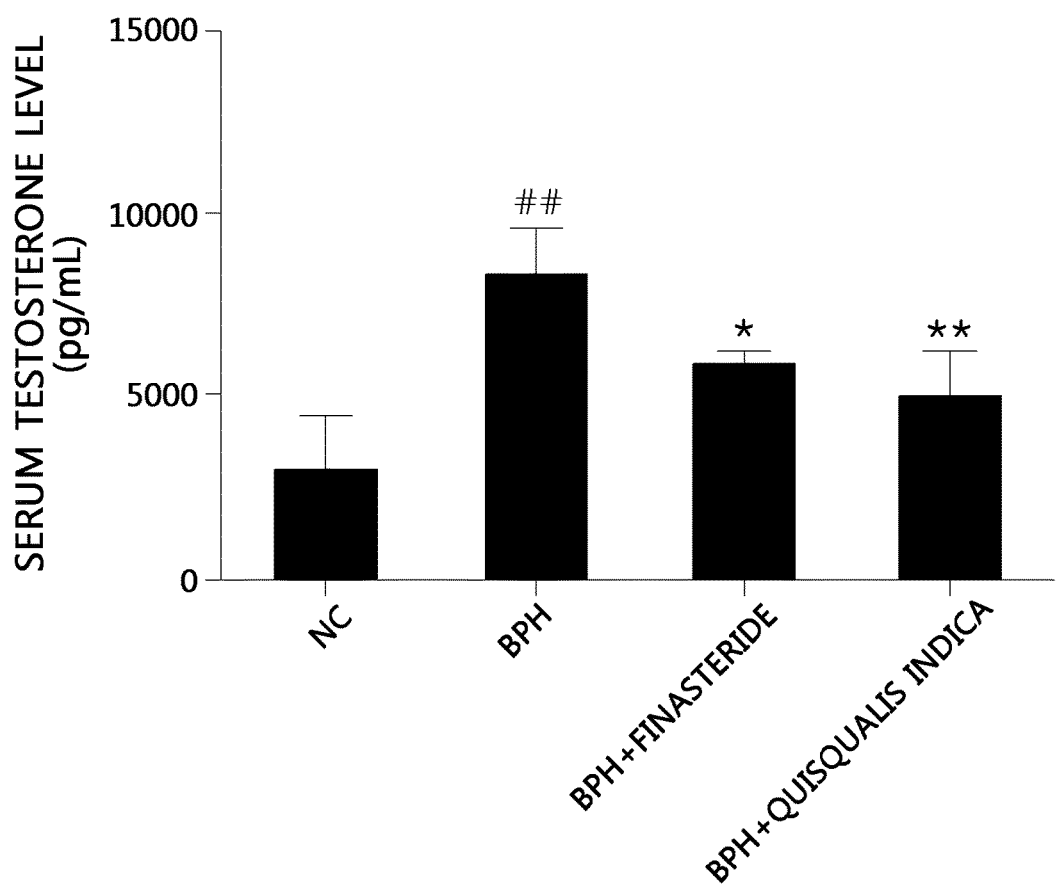
FIG. 3 shows serum testosterone levels in prostatic hyperplasia animal models treated with the *Quisqualis indica* extract.

FIG. 3 shows serum testosterone levels in prostatic hyperplasia animal models treated with the *Quisqualis indica* extract. As can be seen from FIG. 3, the testosterone levels in the group administered with the *Quisqualis indica* extract were significantly reduced.

Example 6

Histopathological Changes of Prostate

The prostate dissected after the end of the experiment was fixed with 10% neutral buffered formalin for 24 hours, followed by paraffin embedding. The embedded tissue was sliced 4 μm in thickness to create a section, which was stained with hematoxylin (Sigma-Aldrich, USA) and eosin Y (Sigma-Aldrich), mounted in mounting medium, and examined using optical microscope.

Figure 4:
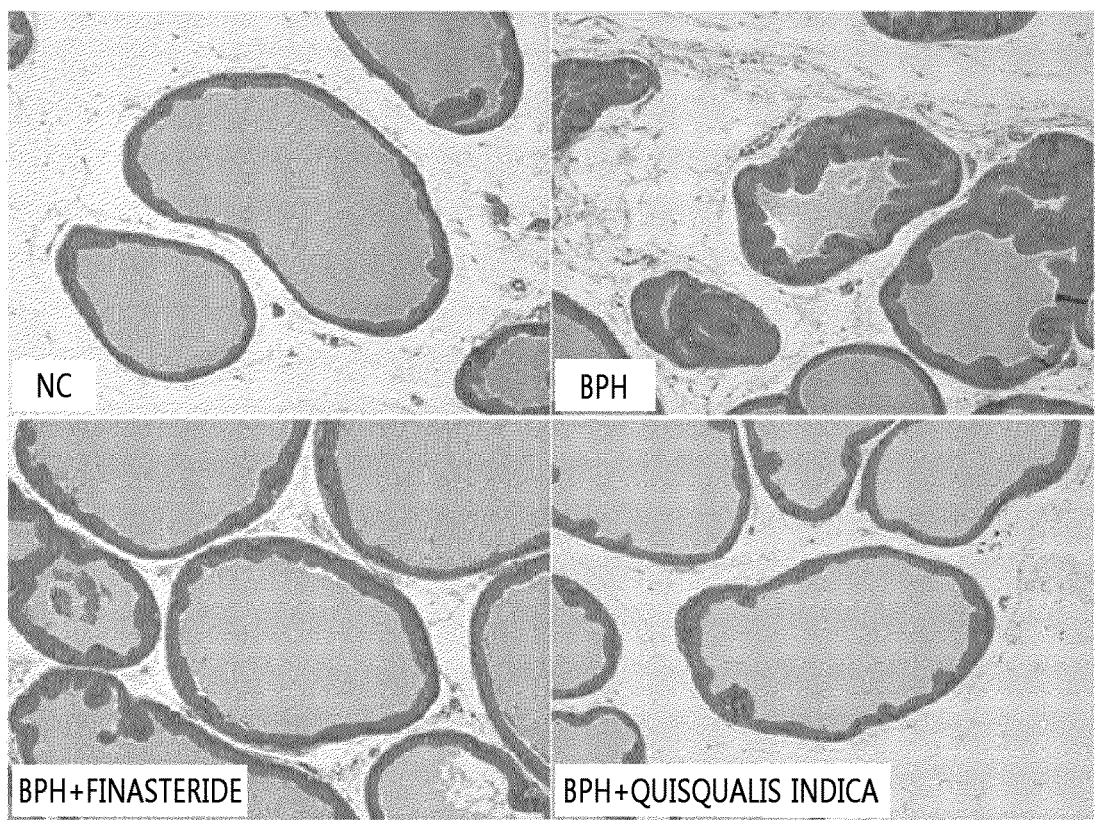
FIG. 4 shows histopathological changes of prostate in prostatic hyperplasia animal models treated with the *Quisqualis indica* extract.

FIG. 4 shows histopathological changes of prostate in prostatic hyperplasia animal models treated with the *Quisqualis indica* extract. As can be seen from FIG. 4, the height and number of epithelial cells greatly increased in the induced prostatic hyperplasia group, while a reduction in epithelial hyperplasia was observed in the group administered with *Quisqualis indica* extract.

Example 7

Serum ALT and AST Measurements

To evaluate the toxicity of the *Quisqualis indica* extract in the prostatic hyperplasia animal model, the blood separated after the end of the experiment was centrifugally separated at 12,000 rpm for 20 minutes, the supernatant was harvested and general hepatotoxicity indices, ALT (alanine transaminase) and AST (aspartate transaminase) levels in serum were measured.

Figure 5:
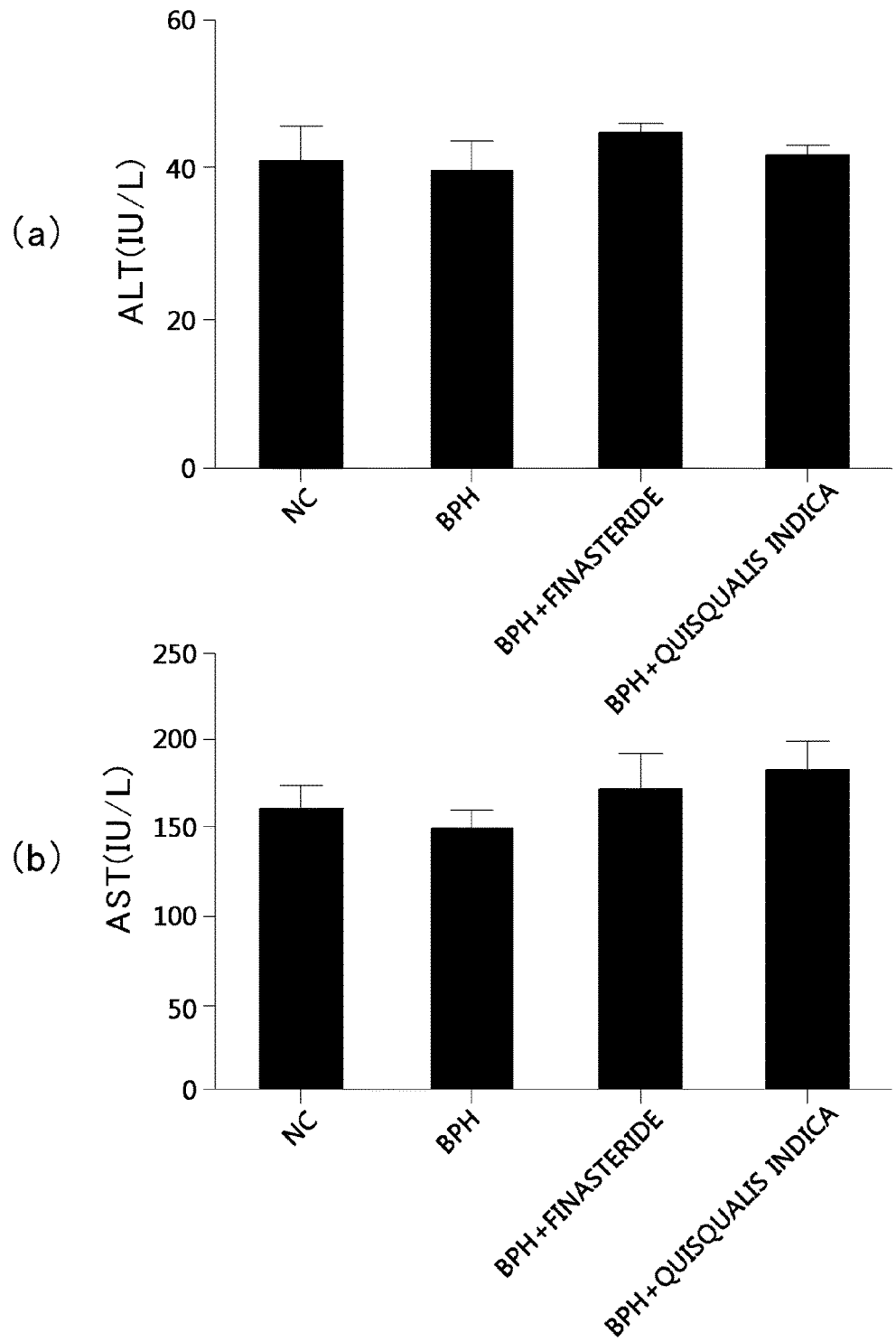
FIG. 5 shows evaluation results of toxicity in prostatic hyperplasia animal models treated with the *Quisqualis indica* extract.

FIG. 5 shows evaluation results of toxicity in prostatic hyperplasia animal models treated with the *Quisqualis*

*indica* extract. As can be seen from FIG. 5, when compared to the normal control group, no significant change in ALT and AST was observed in both the induced prostatic hyperplasia group and the *Quisqualis indica* extract administered group.

Interpretation of Results

According to the examples, testosterone propionate (TP) was subcutaneously injected into white rats for 4 weeks to induce prostatic hyperplasia, and the *Quisqualis indica* extract and finasteride which is being used to treat prostatic hyperplasia were administered for 4 weeks. After the end of medication administration, changes were measured as below.

(1) As a result of comparison of the weight of prostate taken from the sacrificed rats, reductions in prostate weight were found in the group administered with the *Quisqualis indica* extract as compared to the group with TP-induced prostatic hyperplasia, and this showed a similar effect to the group administered with finasteride used to treat prostatic hyperplasia.

(2) Furthermore, following medication administration, as a result of comparison of changes in dihydrotestosterone (DHT) causing prostatic hyperplasia, DHT levels in the group administered with the *Quisqualis indica* extract were significantly reduced, and showed a similar effect to finasteride.

(3) According to the histopathological analysis results of prostate, epithelial hyperplasia observed in the induced prostatic hyperplasia group was reduced after administration of the *Quisqualis indica* extract.

Accordingly, the *Quisqualis indica* extract of the present disclosure has effects on the reduction of prostate weight, DHT which is a factor causing benign prostatic hyperplasia, and prostate epithelial hyperplasia, and thus can be an effective drug for treating prostatic hyperplasia.

Preparation

Preparation examples of the composition of the present disclosure are provided below.

Preparation Example 1

Manufacture of Pharmaceutical Preparation 1-1. Preparation of Powder 2 g of the extract of example 1 of the present disclosure
1 g of lactose The ingredients were mixed and filled in hermetic packaging to prepare powder.

1-2. Preparation of Tablet 100 mg of the extract of example 1 of the present disclosure
100 mg of corn starch
100 mg of lactose
2 mg of magnesium stearate After mixing the ingredients, tableting was performed according to the common tablet preparation method to prepare tablet.

1-3. Preparation of Capsule 100 mg of the extract of example 1 of the present disclosure
100 mg of corn starch
100 mg of lactose
2 mg of magnesium stearate After mixing the ingredients, gelatin capsule was filled according to the common capsule preparation method to prepare capsule.

Preparation Example 2

Manufacture of Food 2-1. Preparation of Cookies and Flour Based Food 0.5-5.0 parts by weight of the extract of example 1 of the present disclosure was added to flour, and bread, cakes, cookies, crackers and noodles were produced using this mixture to produce health enhancing food.

2-2. Preparation of Dairy Product 5-10 parts by weight of the extract of example 1 of the present disclosure was added to milk, and various dairy products such as butter and ice cream were produced using the milk.

Preparation Example 3

Manufacture of Beverage 1000 mg of extract of example 1 of the present disclosure
1000 mg of citric acid
100 g of oligosaccharide
2 g of concentrated Japanese apricot solution
1 g of taurine purified water to 900 ml in total According to the common health beverage manufacturing method, the ingredients were mixed and heated while shaking at 85° C. for about 1 hour to prepare a solution, which was filtered and put in 2l sterilized container, followed by hermetical sealing and sterilization, and cold storage, and was used to produce the health food of the present disclosure.

The present disclosure has been hereinabove described with regard to the preferred embodiments. It should be understood by those having ordinary skill in the technical field pertaining to the present disclosure that the present disclosure may be embodied in modified form without departing from the essential features of the present disclosure. Therefore, the disclosed embodiments should be considered from the illustrative point of view, not the limitative point of view. The scope of the present disclosure is found in the appended claims, not in the foregoing description, and it should be interpreted that all differences within its equivalent scope are included in the present disclosure.

The invention claimed is:

1. A method of treating prostatic hyperplasia, comprising administering a *Quisqualis indica* extract as an active ingredient to a subject in need thereof, wherein the *Quisqualis indica* extract comprises quisqualic acid and fatty oil, and wherein the *Quisqualis indica* extract is orally administered to the subject.

2. The method according to claim 1, wherein the *Quisqualis indica* extract is extracted with water, lower alcohol having 1 to 4 carbon atoms, or their mixed solvent.

3. The method according to claim 1, wherein the *Quisqualis indica* extract has effects on the reduction of prostate weight, dihydrotestosterone (DHT) that is a factor causing prostatic hyperplasia, and prostate epithelial hyperplasia.

4. The method according to claim 1, wherein the *Quisqualis indica* extract is comprised in a food composition, and the administration of the *Quisqualis indica* extract is carried out by orally administering the food composition to the subject.

5. The method according to claim 1, wherein the *Quisqualis indica* extract is comprised in a pharmaceutical composition, and the administration of the *Quisqualis indica* extract is carried out by orally administering the pharmaceutical composition to the subject.

* * * * *